(12) United States Patent
Ni et al.

(10) Patent No.: US 11,213,493 B2
(45) Date of Patent: Jan. 4, 2022

(54) TOPICAL PREPARATION CONTAINING VITAMIN K1 AND PREPARATION METHOD THEREOF

(71) Applicant: YANGZIJIANG PHARMACEUTICAL GROUP SHANGHAI HAINI PHARMACEUTICAL CO., LTD., Shanghai (CN)

(72) Inventors: Haihua Ni, Shanghai (CN); Xinguo Jiang, Shanghai (CN); Feng Jiang, Shanghai (CN); Yun Xu, Shanghai (CN); Xin Pan, Shanghai (CN); Weihong Zhuang, Shanghai (CN)

(73) Assignee: YANGZIJIANG PHARMACEUTICAL GROUP SHANGHAI HAINI PHARMACEUTICAL CO., LTD., Shanghai (CN)

( * ) Notice: Subject to any disclaimer, the term of this patent is extended or adjusted under 35 U.S.C. 154(b) by 0 days.

(21) Appl. No.: 17/042,916

(22) PCT Filed: Nov. 4, 2019

(86) PCT No.: PCT/CN2019/115217
§ 371 (c)(1),
(2) Date: Sep. 29, 2020

(87) PCT Pub. No.: WO2020/093956
PCT Pub. Date: May 14, 2020

(65) Prior Publication Data
US 2021/0015766 A1 Jan. 21, 2021

(30) Foreign Application Priority Data
Nov. 7, 2018 (CN) .......................... 201811321605.5

(51) Int. Cl.
| *A61K 31/122* | (2006.01) |
| *A61K 9/00* | (2006.01) |
| *A61K 9/06* | (2006.01) |
| *A61K 47/10* | (2017.01) |
| *A61K 47/18* | (2017.01) |
| *A61K 47/46* | (2006.01) |

(52) U.S. Cl.
CPC .......... *A61K 31/122* (2013.01); *A61K 9/0014* (2013.01); *A61K 9/06* (2013.01); *A61K 47/10* (2013.01); *A61K 47/18* (2013.01); *A61K 47/46* (2013.01)

(58) Field of Classification Search
None
See application file for complete search history.

(56) References Cited

U.S. PATENT DOCUMENTS

2010/0303935 A1* 12/2010 Squires ................ A61K 36/185
424/726

FOREIGN PATENT DOCUMENTS

| CN | 1435263 A | 8/2003 | |
| CN | 1547475 A | 11/2004 | |
| CN | 109172518 A | 1/2019 | |
| EP | 2712613 A1 * | 4/2014 | .......... A61K 31/404 |
| EP | 2712613 A1 | 4/2014 | |
| JP | 2013253078 A * | 12/2013 | |
| WO | 2016131041 A1 | 8/2016 | |

OTHER PUBLICATIONS

Xue Dong et al., Clinical efficacy of vitamin K1 cream on cetuximab-induced skin toxicity, Oncology Progress, Nov. 2013, pp. 587-591 and 595, vol. 11, No. 6.
Bingbing Pan et al., Progress on Study of Transdermal Therapeutic System, China Practical Medicine, Jul. 2009, pp. 241-244, vol. 4, No. 20.
Yue Wei et al., Research Progress of Cataplasma, Guiding Journal of Traditional Chinese Medicine and Pharmacology, Jun. 2017, pp. 57-59 and 62, vol. 23, No. 11.

* cited by examiner

*Primary Examiner* — Jennifer A Berrios
(74) *Attorney, Agent, or Firm* — Bayramoglu Law Offices LLC

(57) ABSTRACT

A topical preparation containing vitamin K1 and a preparation method thereof are provided. The topical preparation includes the following components in weight percentage: 0.01-5% of vitamin K1, 0.1-25% of a transdermal enhancer and 70-99% of a matrix for the topical preparation. The transdermal enhancer is composed of urea, menthol and *Eucalyptus* oil in a mass ratio of (5-6):(2-3):(1-3). The topical preparation containing vitamin K1 can be used to treat moderate and severe skin toxicity caused by anti-tumor drugs related to epidermal growth factor receptor (EGFR), can effectively treat diseases such as acne-like rash, pruritus, red swelling, dry skin and mucositis caused by EGFR-related anti-tumor drugs, and can ensure the continued treatment with anti-EGFR targeting drugs. It can increase the possibility of vitamin K1 reaching focus sites in the dermal layer through the stratum corneum, and can rapidly alleviate moderate and severe skin diseases caused by EGFR-related anti-tumor drugs.

8 Claims, 1 Drawing Sheet

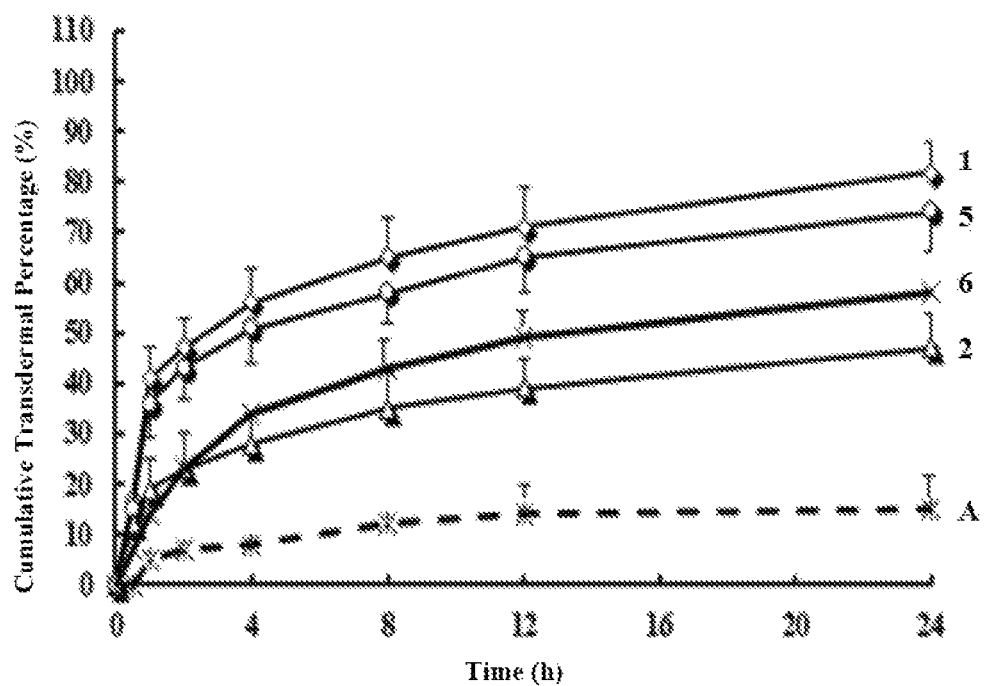

TOPICAL PREPARATION CONTAINING VITAMIN K1 AND PREPARATION METHOD THEREOF

CROSS REFERENCE TO THE RELATED APPLICATIONS

This application is the national phase entry of International Application No. PCT/CN2019/115217, filed on Nov. 4, 2019, which is based upon and claims priority to Chinese Patent Application No. 201811321605.5, filed on Nov. 7, 2018, the entire contents of which are incorporated herein by reference.

TECHNICAL FIELD

The present invention belongs to the technical field of pharmaceutical preparations, and more particularly, relates to a topical preparation containing vitamin K1 and a preparation method thereof.

BACKGROUND

Tumors are a significant health concern for the human population. No effort has been spared to find the best way to treat tumors. In recent years, with a deeper understanding the mechanism of tumors and gene molecular classification, the research of target drugs has become main focus in the field of tumor treatment, and has been especially valued by the medical community. More and more anti-tumor molecular target drugs showing efficacy in treating tumors have been used in clinical practice. Anti-tumor molecular target drugs mainly include afatinib, erlotinib, gefitinib, cetuximab and trastuzumab antibody-drug conjugates, and the target drugs have made breakthroughs in treating tumors, substantially improving the life expectancy of patients. Among the numerous target drugs, inhibitors, or monoclonal antibodies targeting epidermal growth factor receptor (EGFR), are most widely used. However, anti-EGFR target drugs typically have an adverse reaction: moderate to severe skin toxicity.

At present, the mechanism of skin rash caused by anti-EGFR targeted drugs is not fully understood. An interference of epidermal growth signal transduction pathway in follicles and interfollicular cells is speculated to be key component factor for the cause of rash. Other studies have shown that EGFR is expressed in keratinocytes, sebaceous glands, exocrine glands, hair follicles and epithelial adipose layer, and these cells mainly reside in the basal layer of the skin. Inhibition of EGFR can affect the proliferation, differentiation, metastasis and adhesion of glial cells, while anti-EGFR drugs increase the expression of cycle-dependent kinase inhibitors P27, keratin-1, signal transcription and transcription activator-3 in the basal layer cells, which results in growth arrest and premature maturation and differentiation of basal keratinocytes, accompanied by the release of neutrophils. This further leads to keratinocyte apoptosis and accumulation under the epidermis, which results in skin damage. This may thus explain why the skin rash associated with anti-EGFR targeted drugs mainly appears in the upper dermis, focusing near the follicles, which leads to follicle rupture and mixed inflammatory reaction on epithelial spinous layer. Although the occurrence of skin toxicity is rarely life-threatening, it may seriously affect the quality of life of patients, and even result in the individual discontinuing treatment.

Clinically, antibiotics and steroids are mainly used for treating skin toxicity caused by anti-EGFR drugs, but there are still uncertainties and drawbacks associated with the use of these drugs. First, the effect of a single drug treatment is limited, and patients usually need to use antibiotics and corticosteroids in combination. Second, the medication cycle is long, and the symptoms of patients only improve after 2-3 weeks of medication, which is especially uncomfortable for tumor patients with a large area skin toxicity. And because skin toxicity must be treated and re-treated, it may add to and compound diminution of both quality of life and the financial security of patients. Therefore, there is an urgent need for a rapid, effective and safe drug to treat the skin toxicity caused by anti-EGFR targeted drugs.

Vitamin K, also known as coagulation vitamin, has a phylloquinone bioactivity, including K1, K2, K3, K4 and other types. K1 and K2 are natural fat-soluble vitamins. K3 and K4 are synthetic water-soluble vitamins. Among them, vitamin K1 has the highest medicinal value. At present, only the injection of vitamin K1 is available on the market in China, which is mainly used for hemorrhagic diseases caused by vitamin K deficiency.

Dong Xue et al. published a paper entitled "*clinical efficacy of vitamin K1 cream on cetuximab-induced skin toxicity*". This paper discussed an effect of 0.1% vitamin K1 cream on cetuximab-induced skin toxicity in patients with colorectal cancer. The results showed that 0.1% vitamin K1 could relieve the symptoms of skin itching and dry skin of patients with colorectal cancer treated with cetuximab and suffering from skin toxicity. However, an overall effective rate of vitamin K1 cream is low. The main reason is because vitamin K1 is not easy to penetrate stratum corneum, and it is difficult to reach the dermis of a target site of skin rash, which limits further application of vitamin K1 in clinical application.

However, it remains an urgent problem to develop a topical preparation of vitamin K1 with high absorption rate, good therapeutic effect and stability against the skin toxicity caused by anti-EGFR drugs.

SUMMARY

The present invention aims to provide a topical preparation containing vitamin K1 for a treatment of related skin toxicity reactions caused by anti-EGFR targeted drugs. The topical preparation includes a vitamin K1 cream and a vitamin K1 gel. The prescription topical preparation can promote the vitamin K1 to penetrate through cuticle and be absorbed, improving curative effect and increasing stability of vitamin K1.

The related skin toxicity caused by the anti-EGFR targeted drugs of the present invention mainly refers to the skin toxicity reactions caused by using one or more of the following drugs, including small molecule anti-EGFR inhibitors or anti-EGFR monoclonal antibodies. These drugs mainly include: afatinib, erlotinib, gefitinib, lapatinib, vandetanib, trastuzumab, trastuzumab antibody-drug conjugates, cetuximab, panitumumab pertuzumab and others.

In order to achieve the above purpose, the present invention adopts the following technical scheme.

The present invention provides a topical preparation containing vitamin K1, including the following components in weight percentage:

0.01-5% of vitamin K1, 0.1-25% of a transdermal enhancer and 70-99% of a matrix for the topical preparation, wherein the transdermal enhancer is at least one selected from the group consisting of urea, azone, propylene glycol, ethanol, clove oil, *Eucalyptus* oil, menthol, camphor and borneol.

Preferably, a weight percentage of the urea used alone as the transdermal enhancer is 0.1-25%, a weight percentage of the azone used alone as the transdermal enhancer is 0.1-10%, a weight percentage of the propylene glycol used alone as the transdermal enhancer is 0.1-25%, a weight percentage of the ethanol used alone as the transdermal enhancer is 1-25%, a weight percentage of the clove oil used alone as the transdermal enhancer is 0.1-10%, a weight percentage of the *Eucalyptus* oil used alone as the transdermal enhancer is 0.1-10%, a weight percentage of the menthol used alone as the transdermal enhancer is 0.1-10%, a weight percentage of the camphor used alone as the transdermal enhancer is 0.1-10%, and a weight percentage of the borneol used alone as the transdermal enhancer is 0.1-10%.

More preferably, the weight percentage of the urea used alone as the transdermal enhancer is 0.5-10%, the weight percentage of the azone used alone as the transdermal enhancer is 0.5-5%, the weight percentage of the propylene glycol used alone as the transdermal enhancer is 1-10%, the weight percentage of the ethanol used alone as the transdermal enhancer is 2-15%, the weight percentage of the clove oil used alone as the transdermal enhancer is 0.5-5%, the weight percentage of the *Eucalyptus* oil used alone as the transdermal enhancer is 0.5-5%, the weight percentage of the menthol used alone as the transdermal enhancer is 0.5-5%, the weight percentage of the camphor used alone as the transdermal enhancer is 0.5-5%, and the weight percentage of the borneol used alone as the transdermal enhancer is 0.5-5%.

More preferably, the transdermal enhancer is composed of the urea, the menthol and the *Eucalyptus* oil in a mass ratio of (5-6):(2-3):(1-3).

The present invention also provides a cream preparation containing vitamin K1, including the following components in weight percentage:

0.01-5% of vitamin K1, 0.1-25% of a transdermal enhancer, 1-25% of a cream matrix, 0.2-10% of an emulsifier, 2-20% of a humectant, 0.05-2% of an antioxidant, 0.01-1% of a preservative and 10-72% of water, wherein the transdermal enhancer is composed of the urea, the menthol and the *Eucalyptus* oil in a mass ratio of (5-6):(2-3):(1-3).

Preferably, the cream matrix is at least one selected from the group consisting of isostearic acid, stearic acid, hexadecanol, octadecanol, glyceryl monostearate, white vaseline, lanolin and liquid paraffin.

Preferably, the emulsifier is at least one selected from the group consisting of sodium dodecyl sulfate, polysorbate 60, polysorbate 80, polyethylene glycol hydroxystearate, polyethoxylated castor oil, ethylene oxide or propylene oxide copolymer, stearoyl polyethylene glycol-32 glyceride, lauroyl polyethylene glycol-32 glyceride, propylene glycol monooctanoate and octyl acetyl polyethylene glycol-8 glyceride.

Preferably, the humectant is at least one selected from the group consisting of glycerol, propylene glycol and sorbitol. The antioxidant is at least one selected from the group consisting of butyl hydroxyanisole, dibutylhydroxytoluene, propyl gallate, tert-butylhydroquinone, sodium sulfite, sodium bisulfite, sodium pyrosulfite and sodium thiosulfate. The preservative is at least one selected from the group consisting of hydroxyphenyl esters, trichloro tert butyl alcohol, benzyl alcohol, phenylethanol, chlorhexidine acetate, benzalkonium chloride, thiomersal and quaternary ammonium cationic surfactants.

The present invention also provides a gel preparation containing vitamin K1, including the following components in weight percentage:

0.01-5% of vitamin K1, 0.1-25% of a transdermal enhancer, 0.5-10% of a gel matrix, 0.1-10% of a thickener, 2-20% of a humectant, 0.05-2% of an antioxidant, 0.01%-1% of a preservative and 40%-80% of water, wherein the transdermal enhancer is composed of the urea, the menthol and the *Eucalyptus* oil in a mass ratio of (5-6):(2-3):(1-3).

Preferably, the gel matrix is at least one selected from the group consisting of gelatin, Carbopol 934P, polyethylene glycol 300, methyl cellulose, sodium carboxymethyl cellulose and hydroxypropyl methylcellulose; the thickener is at least one selected from the group consisting of xanthan gum, carrageenan and Brunei gum.

Preferably, the gel matrix is composed of Carbopol 934P and polyethylene glycol 300 in a mass ratio of (1-3):(2-3).

Preferably, the Carbopol 934P can be replaced by Carbopol 940, Carbopol 941 and Carbopol 974P.

Preferably, the thickener is at least one selected from the group consisting of xanthan gum, carrageenan and Brunei gum.

Preferably, the humectant is at least one selected from the group consisting of glycerol, propylene glycol and sorbitol. The antioxidant is at least one selected from the group consisting of butyl hydroxyanisole, dibutyl hydroxytoluene, propyl gallate, tert-butylhydroquinone, sodium sulfite, sodium bisulfite, sodium pyrosulfite and sodium thiosulfate. The preservative is at least one selected from the group consisting of hydroxyphenyl esters, trichloro tert butyl alcohol, benzyl alcohol, phenylethanol, chlorhexidine acetate, benzalkonium chloride, thiomersal and quaternary ammonium cationic surfactants.

The topical preparation containing vitamin K1 is made into cream preparation and gel preparation. A pH value of the cream preparation or the gel preparation containing vitamin K1 is 4.0-8.0, preferably 5.0-7.0.

At present, it is found that vitamin K1 can help to relief the symptoms of pruritus and dry skin caused by cetuximab treatment in patients with colorectal cancer. However, vitamin K1 is a kind of fat-soluble vitamin, which is insoluble in water and has poor transdermal absorption. It has no obvious effect on relieving the symptoms of pruritus and dry skin in skin toxicity reaction. The topical preparation containing vitamin K1 provided by the present invention is added with a transdermal enhancer to solve the problem of poor transdermal absorption, and has good therapeutic effect on acne-like rash, pruritus, red swelling, dry skin and mucositis caused by anti-epidermal growth factor receptor (EGFR) targeted drugs including afatinib, erlotinib, gefitinib, lapatinib, vandetanib, trastuzumab, trastuzumab antibody-drug conjugates, cetuximab, panitumumab and pertuzumab, which can extend use period and adaptability of the anti-tumor drugs for tumor patients.

The transdermal enhancer provided by the present invention is urea, azone, propylene glycol, ethanol, clove oil, *Eucalyptus* oil, menthol, camphor and borneol. When the substance listed above is used alone as the transdermal enhancer, the effect of transdermal promotion is limited. The inventor has performed extensive experiments, however, and found that the transdermal enhancer composed of the urea, the menthol and the *Eucalyptus* oil in a mass ratio of (5-6):(2-3):(1-3) can obviously and effectively improve the transdermal absorption of vitamin K1, and can effectively treat acne-like rash, pruritus, red swelling, dry skin and mucositis caused by anti-tumor drugs related to EGFR, which can ensure the continuous treatment using anti-EGFR targeted drugs.

Further, the inventor also found that the transdermal enhancer composed of the urea, the menthol and the *Eucalyptus* oil in the mass ratio of (5-6):(2-3):(1-3) combined with vitamin K1 can prevent ultraviolet radiation from inducing a toxic skin inflammation.

In addition, the inventor also found that the topical preparation containing vitamin K1 prepared by the present invention is made into a gel, which not only has advantages in treating skin toxicity caused by anti-epidermal growth factor receptor (EGFR) targeted drugs, but also has a function of promoting wound healing. After testing and analysis, a possible reason is that the present invention adopts the gel matrix composed of Carbopol 934P and polyethylene glycol 300 in a mass ratio of (1-3):(2-3). Carbopol 934P is a copolymer of acrylic acid cross-linked polymer and polyalkyl sucrose or polyalkyl pentaerythritol, Carbopol molecule has a large number of carboxyl groups, its ionization equilibrium varies with pH value, and the molecule is cross-linked; polyethylene glycol 300 molecule is linear and has good hygroscopicity, and the change of pH value and temperature have no effect on the polyethylene glycol 300. When the polyethylene glycol 300 and the Carbopol 934P are mixed, an arrangement and combination of them are affected by van der Waals force. The polyethylene glycol 300 can fill a space gap of the Carbopol 934P, which makes it less susceptible to temperature and pH value change, so as to increase stability of the Carbopol 934P. At the same time, after mixing, arrangement and combination of the Carbopol 934P having cross-linked molecular structure and the polyethylene glycol 300 having linear molecular structure, because the polyethylene glycol 300 has certain hygroscopicity, it forms a dense hydrogel film with the Carbopol 934P having cross-linked molecular structure after moisture absorption, which can prevent bacteria from growing and promote wound healing.

Compared with the prior art, the present invention has the following advantages:

(2) The topical preparation containing vitamin K1 provided by the present invention contains a transdermal enhancer, which can effectively promote the vitamin K1 to penetrate through the stratum corneum to reach the lesion site of dermis, so as to achieve a purpose of synergistic effect. The topical preparation containing vitamin K1 has significant effect on treating and preventing skin toxicity caused by anti-epidermal growth factor receptor (EGFR) targeted drugs.

(2) When the topical preparation containing vitamin K1 provided by the present invention is made into gel, it has advantages of being moist, cool and no greasy feeling, and is suitable for applying to whole body, and is more conducive to the efficacy of drugs.

BRIEF DESCRIPTION OF THE DRAWINGS

FIGURE is a diagram showing a cumulative transdermal percentage of an external cream preparation containing vitamin K1, wherein 1 is a cumulative transdermal percentage curve of the external cream preparation containing vitamin K1 prepared in embodiment 1; 2 is a cumulative transdermal percentage curve of the external cream preparation containing vitamin K1 prepared in embodiment 2; 5 is a cumulative transdermal percentage curve of the external cream preparation containing vitamin K1 prepared in embodiment 5; 6 is a cumulative transdermal percentage curve of the external cream preparation containing vitamin K1 prepared in embodiment 6; and A is an external cream preparation containing vitamin K1 without transdermal enhancer.

DETAILED DESCRIPTION OF THE EMBODIMENTS

The above contents of the present invention will be further described in detail through the specific embodiments below. However, it should not be understood that the scope of the above subject matter of the present invention is limited to the following embodiments.

Embodiments 1-11. Cream Preparation Containing Vitamin K1

A cream preparation containing vitamin K1 is prepared according to embodiments 1-11 shown in Table 1.

TABLE 1

Formulation of the cream preparation containing vitamin K1 (w/w %)

| Component | Embodiment 1 | Embodiment 2 | Embodiment 3 | Embodiment 4 | Embodiment 5 | Embodiment 6 | Embodiment 7 | Embodiment 8 | Embodiment 9 | Embodiment 10 | Embodiment 11 |
|---|---|---|---|---|---|---|---|---|---|---|---|
| vitamin K1 | 0.01 | 0.2 | 0.5 | 2 | 5 | 0.1 | 1 | 3 | 3 | 3 | 3 |
| urea | 0.1 | 10 | 25 | 1 | — | — | — | — | 15 | 11 | 12 |
| azone | 10 | 0.1 | — | 3 | 1 | — | — | — | — | — | — |
| *eucalyptus* oil | — | — | — | 0.1 | 10 | 1 | — | — | 3 | 4 | 6 |
| clove oil | — | — | — | — | 0.1 | 1 | 10 | — | — | — | — |
| menthol | — | — | — | — | 2 | 10 | 1 | 0.1 | 6 | 5 | 6 |
| camphor | 1 | 2 | 0.1 | 10 | — | — | — | — | — | — | — |
| borneol | 1 | — | — | — | 0.1 | — | — | 10 | — | — | — |
| isostearic acid | 10 | — | 5 | — | 15 | — | — | 25 | — | — | — |
| stearic acid | 5 | 10 | 1 | 15 | 1 | 20 | 10 | 5 | 5 | 5 | 5 |
| hexadecanol | 1 | — | — | 10 | 0.5 | — | — | — | 1 | 1 | 1 |
| octadecanol | — | — | 10 | 1 | 0.5 | — | — | — | — | — | — |
| glycerin monostearate | 0.5 | 5 | 2 | — | 10 | — | 1 | 3 | 5 | 5 | 5 |
| white vaseline | 10 | 0.1 | 1 | 5 | 2 | — | — | 3 | — | — | — |
| lanolin | — | 2 | 1 | — | 0.1 | 5 | 10 | — | — | — | — |
| liquid paraffin | 8 | 10 | 20 | 12 | 15 | 2 | 5 | 1 | 10 | 10 | 10 |
| dibutyl hydroxytoluene | 0.05 | — | 1 | — | 2 | — | — | — | — | — | — |

TABLE 1-continued

Formulation of the cream preparation containing vitamin K1 (w/w %)

| Component | Embodiment 1 | Embodiment 2 | Embodiment 3 | Embodiment 4 | Embodiment 5 | Embodiment 6 | Embodiment 7 | Embodiment 8 | Embodiment 9 | Embodiment 10 | Embodiment 11 |
|---|---|---|---|---|---|---|---|---|---|---|---|
| butyl hydroxyanisole | — | 1 | — | 0.05 | — | 2 | — | — | — | — | — |
| propyl gallate | 0.05 | 1 | — | — | — | — | 2 | — | — | — | — |
| tert-butyl-hydroquinone | 1 | — | 0.05 | 1 | — | — | — | 2 | 2 | 2 | 2 |
| polysorbate 60 | 0.1 | 1 | 2 | 5 | — | — | — | — | 1 | 1 | 1 |
| polysorbate 80 | 5 | 2 | 1 | 0.1 | — | — | — | — | — | — | — |
| sodium dodecyl sulfate | — | — | — | — | 3 | 0.1 | 1 | 0.5 | — | — | — |
| glycerol | 2 | 5 | 20 | — | — | 2 | — | — | — | — | — |
| sorbitol | 2 | — | — | 20 | 5 | — | — | — | — | — | — |
| propylene glycol | — | — | — | — | — | 2 | 5 | 20 | 10 | 10 | 10 |
| triethanolamine | 0.5 | 1 | 0.1 | 1.5 | 0.1 | 2 | 1 | 0.5 | 0.1 | 0.1 | 0.1 |
| benzyl alcohol | — | — | — | — | — | 1 | 2 | 5 | 0.5 | 0.5 | 0.5 |
| methyl paraben | 0.02 | 0.05 | 0.1 | 0.2 | 0.5 | — | — | — | 0.2 | 0.2 | 0.2 |
| ethyl paraben | 0.5 | 0.2 | 0.1 | 0.05 | 0.02 | — | — | — | — | — | — |
| distilled water | 42.07 | 49.35 | 10.0 | 12.95 | 27.08 | 52.79 | 51.0 | 21.9 | 38.2 | 42.2 | 38.2 |

Preparation of Cream Preparation Containing Vitamin K1:

① Preparation of oil phase: a cream matrix is heated to 70-80° C. to melt, followed by stirring to mix evenly, then adding vitamin K1, an antioxidant, a preservative and a fat-soluble transdermal enhancer for dissolving and mixing evenly to obtain a mixed solution A;

② Preparation of aqueous phase: an emulsifier, an antioxidant and a water-soluble transdermal enhancer are mixed, followed by adding into water, heating to 70-80° C., stirring, dissolving and mixing to obtain a mixed solution B;

③ The mixed solution A of step ① is added into the mixed solution B of step ②, under a constant temperature of 70-80° C., stirring is performed for 30 min, followed by cooling to 40° C. while stirring, adding menthol, camphor or borneol, stirring at a constant temperature of 40° C. for 15 min, adding a pH regulator to adjust pH value to 5.0-7.0, stirring and cooling to 20-30° C. while stirring.

Embodiments 12-22. Gel Containing Vitamin K1

A gel preparation containing vitamin K1 is prepared according to embodiments 12-22 shown in Table 2.

TABLE 2

Formulation of the gel preparation containing vitamin K1 (w/w %)

| Component | Embodiment 12 | Embodiment 13 | Embodiment 14 | Embodiment 15 | Embodiment 16 | Embodiment 17 | Embodiment 18 | Embodiment 19 | Embodiment 20 | Embodiment 21 | Embodiment 22 |
|---|---|---|---|---|---|---|---|---|---|---|---|
| vitamin K1 | 0.1 | 1 | 0.5 | 0.01 | 5 | 0.2 | 0.5 | 2 | 3 | 3 | 3 |
| Carbopol 934P | 0.1 | 0.5 | 1 | 5 | — | — | — | — | 6 | 4 | 2 |
| polyethylene glycol 300 | — | — | — | — | — | — | — | — | 4 | 6 | 6 |
| sodium carboxymethyl cellulose | 0.5 | — | — | — | 10 | — | — | — | — | — | — |
| hydroxypropyl methylcellulose | — | 0.1 | — | — | — | 10 | — | — | — | — | — |
| xanthan gum | 0.2 | — | — | — | — | — | 6 | — | — | — | — |
| carrageenan | — | — | 0.3 | — | — | — | — | 8 | — | — | — |
| urea | 25 | 15 | 10 | 5 | 2 | 1 | 0.5 | 0.1 | 15 | 11 | 12 |
| menthol | 0.1 | 1 | 2 | 5 | — | — | — | — | 6 | 5 | 6 |
| camphor | — | — | — | — | 5 | 2 | 1 | 0.1 | — | — | — |
| *eucalyptus* oil | — | — | — | — | — | — | — | — | 3 | 4 | 6 |
| ethanol | 1 | 5 | 10 | 20 | 25 | 10 | 5 | 1 | 1 | 1 | 1 |
| propylene glycol | 25 | 5 | 2 | 0.2 | 0.1 | 2 | 5 | 20 | — | — | — |
| glycerol | — | 1 | 5 | — | — | 2 | 5 | — | 4 | 4 | 4 |
| sodium sulfite | 0.05 | 0.2 | 1 | 2 | — | — | — | — | — | — | — |
| sodium pyrosulfite | — | — | — | 0.05 | 0.2 | 1 | 2 | — | 1 | 1 | 1 |
| sodium thiosulfate | 2 | — | — | — | — | — | 0.05 | 1 | — | — | — |
| methyl paraben | 0.05 | 0.1 | 0.2 | 0.5 | — | — | — | — | — | — | — |
| ethyl paraben | — | — | — | — | 0.05 | 0.1 | 0.2 | 0.5 | 0.1 | 0.1 | 0.1 |
| triethanolamine | 0.1 | 0.5 | 1 | 2 | — | — | — | — | — | — | — |
| distilled water | 45.8 | 70.6 | 67.0 | 60.24 | 52.65 | 71.7 | 75.2 | 67.3 | 56.9 | 52.9 | 58.9 |

Preparation of Gel Preparation Containing Vitamin K1:

① A gel matrix and a thickening agent are added to distilled water and put aside for 8-12 h, followed by adding a water-soluble transdermal enhancer and an antioxidant to obtain a mixed solution A.

② The vitamin K1 and a fat-soluble transdermal enhancer are added into ethanol, followed by stirring, dissolving and mixing well to obtain a mixed solution B;

③ The mixed solution B of step ② is added into the mixed solution A of step ①, followed by stirring and mixing evenly, adding a pH regulator to adjust pH value to 5.0-7.0, and stirring evenly.

Comparative Examples 1-2. Cream Preparation Containing Vitamin K1

The cream preparation containing vitamin K1 is prepared according to comparative example 1 and comparative example 2 as shown in Table 3.

TABLE 3

Formulation of the cream preparation containing vitamin K1 (w/w %)

| Component | Comparative example 1 | Comparative example 2 |
|---|---|---|
| vitamin K1 | 3 | 3 |
| urea | 8 | 6 |
| eucalyptus oil | 2 | 6 |
| menthol | 8 | 6 |
| stearic acid | 5 | 5 |
| hexadecanol | 1 | 1 |
| glycerin monostearate | 5 | 5 |
| liquid paraffin | 10 | 10 |
| tert-butylhydroquinone | 2 | 2 |
| polysorbate 60 | 1 | 1 |
| propylene glycol | 10 | 10 |
| triethanolamine | 0.1 | 0.1 |
| benzyl alcohol | 0.5 | 0.5 |
| methyl paraben | 0.2 | 0.2 |
| distilled water | 44.2 | 44.2 |

The preparation method of the cream preparation containing vitamin K1 is similar to the preparation method of embodiments 1-9.

The comparative example 1 differs from the embodiment 10 in that the transdermal enhancer is composed of urea, menthol and *Eucalyptus* oil in a mass ratio of 4:1:4.

The comparative example 2 differs from the embodiment 10 in that the transdermal enhancer is composed of urea, menthol and *Eucalyptus* oil in a mass ratio of 1:1:1.

Comparative Examples 3-6. Gel Preparation Containing Vitamin K1

The gel preparation containing vitamin K1 is prepared according to comparative example 3, comparative example 4, comparative example 5 or comparative example 6 as shown in Table 4.

TABLE 4

Formulation of the gel preparation containing vitamin K1 (w/w %)

| Component | Comparative Example 3 | Comparative Example 4 | Comparative Example 5 | Comparative Example 6 |
|---|---|---|---|---|
| vitamin K1 | 3 | 3 | 3 | 3 |
| Carbopol 934P | 4 | 4 | 4 | 4 |
| polyethylene glycol 300 | 6 | 6 | 4 | — |
| sodium carboxymethyl cellulose | — | — | — | 6 |
| urea | 8 | — | 11 | 11 |
| menthol | 8 | 20 | 5 | 5 |
| eucalyptus oil | 2 | — | 4 | 4 |
| ethanol | 1 | 1 | 1 | 1 |
| glycerol | 4 | 4 | 4 | 4 |
| sodium pyrosulfite | 1 | 1 | 1 | 1 |
| ethyl paraben | 0.1 | 0.1 | 0.1 | 0.1 |
| distilled water | 54.9 | 52.9 | 52.9 | 52.9 |

The preparation method of the gel preparation containing vitamin K1 is similar to the preparation method of embodiment 12-22.

The comparative example 3 differs from the embodiment 21 in that the transdermal enhancer is composed of urea, menthol and *Eucalyptus* oil in the mass ratio of 4:1:4.

The comparative example 4 differs from the embodiment 21 in that the transdermal enhancer is composed of urea, menthol and *Eucalyptus* oil in a mass ratio of 1:1:1.

The comparative example 5 differs from the embodiment 21 in that the gel matrix is composed of Carbopol 934P and polyethylene glycol 300 in a mass ratio of 1:1.

The comparative example 6 differs from the embodiment 21 in that the gel matrix is composed of Carbopol 934P and sodium carboxymethyl cellulose at a mass ratio 2:3.

Test Example 1: Transdermal Test of Cream Preparation Containing Vitamin K1

1. Test purpose: transdermal tests of cream preparations containing vitamin K1 in embodiments 1, 2, 5 and 6.

2. Test Method:

A modified Franz diffusion cell technique is used. The depilated abdominal rat skin is fixed between two cells. The stratum corneum is facing the supplying cell and the dermis is facing the receiving cell. 1 g of the cream preparations are respectively applied on the skin. The receiving cell contains 18 ml of PBS (pH=7.4) dissolution medium. A rotor speed is adjusted to 75 r/min, and a temperature is controlled at 32±0.5° C. Sampling is performed at 0.5 h, 1 h, 2 h, 4 h, 8 h, 12 h and 24 h, respectively, with 0.5 ml for each sampling. A centrifugation is performed for 10 min at 12000 r/min after shaking well. A supernatant is taken and a concentration of vitamin K1 in the receiving solution is determined by high performance liquid chromatography (HPLC); at the same time, the same volume of heat preservation medium is added. a determination concentration $C_{determination}$ of the drug in the medium at each sampling time point is obtained according to the formula:

$$C_{standard} = C_{determination} + \frac{0.5}{18}\sum_{i=1}^{n-1} C_{determination}$$

Corrected concentration calculation. The cumulative transdermal percentage F(t) is calculated according to the corrected concentration, and a transdermal absorption curve is drawn with F(t) versus time. The cream preparation containing vitamin K1 without transdermal enhancer is used as a control preparation.

In the same way, the tests are stopped after 4 h and 8 h respectively, followed by removing the skin in the diffusion cell, cleaning the residual drug on the surface, drying with filter paper, and weighing. After homogenization, dilution is performed until an appropriate concentration is reached, followed by extracting the vitamin K1 in the skin homogenate twice with dichloromethane, removing the organic solvent with nitrogen in a constant temperature water bath, dissolving the extract with 100 μL of chromatographic mobile phase, determining the concentration of vitamin K1 by HPLC, and comparing the residual amounts of vitamin K1 in different preparations.

3. Test Results:

The transdermal ability of cream preparation containing vitamin K1 can be significantly improved by adding an appropriate amount of transdermal enhancer, as shown in the FIGURE.

It can be seen from the FIGURE that, for the cream preparations containing vitamin K1 prepared in embodiment 1, embodiment 2, embodiment 5 and embodiment 6, the cumulative amount of vitamin K1 penetrating the depilated abdominal rat skin within 24 h is 47-88%, while that for the control preparation without transdermal enhancer, the cumulative amount of vitamin K1 penetrating the depilated abdominal rat skin is 15%. The results show that the cumulative transdermal percentages of the cream preparations containing vitamin K1 prepared by embodiment 1, embodiment 2, embodiment 5 and embodiment 6 increase significantly after adding the transdermal enhancer.

In addition, the residual concentration of vitamin K1 in skin tissue is significantly increased after adding transdermal enhancer. The concentration of vitamin K1 in skin is 3.1-5.5 times that of the control preparation at 8 hours. It is suggested that cream preparation containing vitamin K1 added with various transdermal enhancers can promote the vitamin K1 to penetrate through the stratum corneum and into the dermis in varying degrees, so as to improve the therapeutic effect on the skin toxicity caused by anti-epidermal growth factor receptor (EGFR) targeted drugs.

Test Example 2: Transdermal Test of Topical Preparation Containing Vitamin K1

1. Test purpose: common cream preparation containing vitamin K1, cream preparations containing vitamin K1 prepared in embodiment 1, embodiment 8, embodiment 9, embodiment 10 and embodiment 11 of the present invention; gel preparations containing vitamin K1 prepared in embodiment 12, embodiment 16, embodiment 19, embodiment 20, embodiment 21 and embodiment 22 of the present invention; cream preparations containing vitamin K1 prepared in comparative example 1 and comparative example 2 and gel preparations containing vitamin K1 prepared in comparative example 3 and comparative example 4 of the present invention.

2. Test Method:

2.1 Ex Vivo Drug Transdermal Absorption Experiment

The ex vivo transdermal absorption experiment is performed in an improved Franz non-coated diffusion cell. The depilated abdominal rat skin is fixed between the two cells. The stratum corneum is facing the supplying cell and the dermis is facing the receiving cell. 1 g of the cream preparation or gel preparation containing transdermal enhancer is evenly applied on the stratum corneum of rat skin. After 20 minutes, the cream preparation or gel preparation containing transdermal enhancer is cleaned. A water temperature in the constant temperature bath is set as 32±0.1° C., followed by adding 7 ml of corresponding receiving solution into the receiving cell. The receiving solution is normal saline. The receiving cell is put into the constant temperature bath of ex vivo osmotic diffusion device which has been preheated for 30 minutes, and a stirring speed of the receiving cell is set as 100 r/min.

1 g of the common cream preparation containing 5% vitamin K1 (according to the preparation method of cream preparation containing vitamin K1 in "clinical efficacy of vitamin K1 cream on cetuximab-induced skin toxicity", Dong Xue), the cream preparations containing vitamin K1 prepared in embodiment 1, embodiment 8, embodiment 9, embodiment 10 and embodiment 11 of the present invention, the gel preparations containing vitamin K1 prepared in embodiment 12, embodiment 16, embodiment 19, embodiment 20, embodiment 21 and embodiment 22 of the present invention, the cream preparations containing vitamin K1 prepared in comparative example 1 and comparative example 2 and the gel preparations containing vitamin K1 prepared in comparative example 3 and comparative example 4 of the present invention are respectively added to the supplying cell to perform the ex vivo transdermal diffusion test. The content of vitamin K1 in the receiving cell is determined after 12 h, and the drug concentration in the sample solution is determined by HPLC.

Chromatographic conditions: chromatographic column: Diamonsil C18 (4.6 mm×250 mm, 5 μm); column temperature: 30° C.; mobile phase: absolute ethanol-water (90:10); flow rate: 1.0 mL/min; detection wavelength: 254 nm; injection volume: 20 μL. A peak area normalization method is used to determine the drug concentration and calculate the transdermal percentage of vitamin K1.

3. Test results: the cumulative transdermal percentage of each topical preparation containing vitamin K1 is shown in Table 5.

TABLE 5

Cumulative transdermal percentage % of vitamin K1 in different topical preparations containing vitamin K1

| Sample | Cumulative Transdermal Percentage (%) |
| --- | --- |
| Common cream preparation containing vitamin K1 | 12.34 |
| Embodiment 1 | 72.50 |
| Embodiment 8 | 50.05 |
| Embodiment 9 | 80.23 |
| Embodiment 10 | 87.45 |
| Embodiment 11 | 84.16 |
| Embodiment 12 | 80.42 |
| Embodiment 16 | 61.43 |
| Embodiment 19 | 60.24 |
| Embodiment 20 | 86.74 |
| Embodiment 21 | 88.40 |
| Embodiment 22 | 85.28 |
| Comparative example 1 | 71.83 |
| Comparative example 2 | 70.02 |
| Comparative example 3 | 72.34 |
| Comparative example 4 | 73.56 |

(2) The cumulative transdermal percentages of the cream preparations containing vitamin K1 prepared in embodiment 1, embodiment 8, embodiment 9, embodiment 10 and embodiment 11 of the present invention, and the cumulative transdermal percentages of the gel preparations containing vitamin K1 prepared in embodiment 12, embodiment 16, embodiment 19, embodiment 20, embodiment 21 and embodiment 22 of the present invention are higher than that of the common cream preparation containing vitamin K1, wherein the cream preparation containing vitamin K1 (embodiment 10) having a transdermal enhancer made of urea, menthol and *Eucalyptus* oil with a mass ratio of 5.5:2.5:2 shows the best transdermal effect among all cream preparations, and the cumulative transdermal percentage of the gel preparation containing vitamin K1 (embodiment 21) has the best transdermal effect among all gel preparations. The cumulative transdermal percentage of the gel preparation containing vitamin K1 prepared in embodiment 21 (88.40%) is slightly higher than that of the cream preparation containing vitamin K1 prepared in embodiment 10 (87.45%). The results show that the addition of urea, menthol and *Eucalyptus* oil in a mass ratio of (5-6):(2-3):(1-3) results in a significant effect on transdermal absorption.

(2) The cumulative transdermal percentages of the cream preparations containing vitamin K1 prepared in comparative example 1 and comparative example 2 and the gel preparations containing vitamin K1 prepared in comparative example 3 and comparative example 4 of the present invention are higher than that of the common cream preparation containing vitamin K1, but is equivalent to that of the cream preparations containing vitamin K1 prepared in embodiment 1 and embodiment 8, and even the cumulative transdermal percentages of the topical preparations containing vitamin K1 prepared in comparative examples 1-4 are higher than that of the topical preparations containing vitamin K1 prepared in the embodiments. For example, the transdermal percentage of the preparation prepared in embodiment 8 is 50.05%, the transdermal percentage of the preparation prepared in embodiment 19 is 60.24%, and the transdermal percentage of the preparation prepared in comparative example 4 is 73.56%, which shows that the transdermal effect the transdermal enhancer composed of urea, menthol and *Eucalyptus* oil is better than other transdermal enhancers and their combinations.

Test Example 3. Efficacy Test of External Cream Preparation Containing Vitamin K1

1. Test purpose: pharmacodynamic test is performed on human body with cream preparation containing vitamin K1 of embodiment 10.
2. Test method: six patients with metastatic advanced colorectal cancer are selected, followed by treating with FOLFOX/FOLFIRI and cetuximab in a two-week clinical regimen, and dividing the six patients randomly into two groups. One group is treated with the cream preparation containing vitamin K1, and the other group is treated with common cream preparation containing vitamin K1 (which is obtained according to the preparation method of cream preparation containing vitamin K1 in *"clinical efficacy of vitamin K1 cream on cetuximab-induced skin toxicity"*, Dong Xue) as a control group. The cream preparations are applied twice respectively in the morning and evening for 7 consecutive days.
3. Test Results:
before using cream preparation, the patients have severe acne-like rash, pruritus and red swelling on the upper body and trunk caused by cetuximab, however, after 7-day treatment with cream preparation containing vitamin K1 in embodiment 10 of the present invention, the skin rash on the upper body and trunk of the patients is significantly less than that using the common cream preparation containing vitamin K1 of the control group, the degree of red swelling is reduced, and the itching sensation disappears, showing obvious curative effect.

Test Example 4. Anti Ultraviolet Effect of Topical Preparation Containing Vitamin K1

1. Test purpose: to investigate anti ultraviolet effects of the gel preparation containing vitamin K1 prepared in embodiment 12, embodiment 13, embodiment 14, embodiment 20, embodiment 21, embodiment 22, comparative example 3 and comparative example 4.
2. Test Method:
HaCaT cells and ESF cells are inoculated in 6-well plates with $2 \times 10^5$ cells/well, when the fusion degree of cells is more than 80%, UVB irradiation treatment is started. The cells are divided into 8 groups with three accessory holes repeated, i.e., blank control group (without UVB treatment, medium without the addition of vitamin K1 topical preparation), UVB irradiation group (UVB treatment, medium without the addition of vitamin K1 topical preparation), UVB+vitamin K1 topical preparation (UVB treatment, medium added with different concentrations of the gel preparations containing vitamin K1 prepared in embodiment 12, embodiment 13, embodiment 14, embodiment 20, embodiment 21, comparative example 3 and comparative example 4, where the concentrations of the gel preparations added are 5 μg/ml, 25 μg/ml, 50 μg/ml, respectively, according to vitamin K1 concentration contained therein.

After 24 hours of inoculation, the culture medium is removed, followed by adding phosphate buffered saline (PBS) to clean the cells once, removing the PBS, and then putting the cells into an ultraviolet irradiation box for UVB treatment. A wavelength of UVB irradiation source is 280-320 nm, and a wave peak is 312 nm. An irradiation dose of UVB on HaCaT cells is 20 mJ/cm$^2$, and an irradiation dose of UVB on ESF cells is 60 mJ/cm$^2$, respectively. After irradiation, the cells are added to complete medium for cultivation with vitamin K1 preparation for 24 h, and a supernatant after cell culture is selected for detection of IL-1 content.

IL-1α content in the supernatant after the cell culture is detected by human IL-1α/IL-1F1DuoSet ELISA Kit (R&D system, USA), IL-6 content is detected by human IL-6Duo-Set ELISA Kit (R&D system, USA), and TNF-α content is detected by human TNF-α DuoSet ELISA Kit (R&D system, USA), and the detection is performed based on operation instructions. At the same time, protein content is detected to correct the results, and the protein content is detected by BCA Protein Assay Kit (Beyotime, China).
3. Test Results:
The detection results are shown in Table 6 including content determinations of IL-1α, IL-6 and TNF-α.

TABLE 6

Content determinations of IL-1 a, IL-6 and TNF-a

| | Drug concentration μg/ml | Embodiment 12 | Embodiment 13 | Embodiment 14 | Embodiment 20 | Embodiment 21 | Embodiment 22 | Comparative example 3 | Comparative example 4 | Blank control group | Irradiation group |
|---|---|---|---|---|---|---|---|---|---|---|---|
| IL-1α | 5 | 98.5 | 91.4 | 98.6 | 98.8 | 82.4 | 90.2 | 99.8 | 99.7 | 6.7 | 100 |
| IL-6 | | 98.4 | 90.1 | 99.2 | 98.8 | 86.1 | 89.7 | 98.5 | 99.8 | 10.2 | 100 |

TABLE 6-continued

Content determinations of IL-1 a, IL-6 and TNF-a

| | Drug concentration μg/ml | Embodiment 12 | Embodiment 13 | Embodiment 14 | Embodiment 20 | Embodiment 21 | Embodiment 22 | Comparative example 3 | Comparative example 4 | Blank control group | Irradiation group |
|---|---|---|---|---|---|---|---|---|---|---|---|
| TNF-a | | 98.4 | 95.2 | 97.5 | 97.3 | 95.2 | 88.9 | 99.6 | 99.5 | 16.5 | 100 |
| IL-1α | 25 | 90.6 | 86.1 | 92.7 | 85.6 | 80.1 | 84.6 | 95.1 | 94.3 | 5.7 | 100 |
| IL-6 | | 87.8 | 88.2 | 93.4 | 86.8 | 84.2 | 87.2 | 94.7 | 93.2 | 9.2 | 100 |
| TNF-a | | 88.4 | 89.3 | 93.8 | 85.6 | 78.3 | 80.6 | 92.3 | 90.7 | 15.5 | 100 |
| IL-1α | 50 | 80.3 | 85.2 | 90.2 | 80.7 | 76.2 | 80.4 | 86.3 | 82.2 | 7.7 | 100 |
| IL-6 | | 81.2 | 84.5 | 88.1 | 80.2 | 80.5 | 84.7 | 82.2 | 83.5 | 10.5 | 100 |
| TNF-a | | 80.4 | 85.3 | 87.6 | 80.4 | 75.3 | 78.3 | 84.4 | 85.3 | 14.6 | 100 |

It can be seen from Table 6 that:

(1) Ultraviolet irradiation can increase the expression of proinflammatory cytokines IL-1α, IL-6 and TNF-a in HaCaT cells, which leads to an activation of other inflammatory factors. The activation of inflammatory factors will aggravate an inflammatory reaction caused by the metabolism of chemical agents and anti-tumor chemotherapy drugs, which is not conducive to healing of inflammatory wounds. From the experimental data, we know that an expression of IL-1α in normal HaCaT cells increased significantly after the HaCaT cells are subjected to irradiation treatment, while an expression of IL-la, IL-6 and TNF-α in HaCaT cells decreased significantly with an addition of gel preparations containing vitamin K1 prepared in embodiment 12, embodiment 13, embodiment 14, embodiment 20, embodiment 21 and embodiment 22, and the decreasing degree is more pronounced with the increasing concentration.

(2) The gel preparations containing vitamin K1 prepared in comparative example 3 and comparative example 4 also has a certain anti-UV irradiation effect, and with an increase of vitamin K1 concentration, the anti-UV irradiation effect is better, even higher than that of the gel preparations containing vitamin K1 produced in embodiment 13 and embodiment 14.

(3) According to formulations of the gel preparations containing vitamin K1 prepared in embodiment 12, embodiment 13, embodiment 14, embodiment 20, embodiment 21, embodiment 22, comparative example 3 and comparative example 4, the effects of the gel preparations containing vitamin K1 prepared in embodiment 20, embodiment 21 and embodiment 22 are better than that of embodiment 13 and embodiment 14, and equivalent to that of embodiment 12, wherein, the difference between the gel preparations containing vitamin K1 prepared in comparative example 3 and comparative example 4 is that the transdermal enhancer is composed of urea, menthol and *Eucalyptus* oil in a mass ratio of (5-6):(2-3):(1-3). The results show that the cream preparations and gel preparations containing vitamin K1 prepared in the present invention with the addition of urea, menthol and *Eucalyptus* oil in a mass ratio of (5-6):(2-3):(1-3) can inhibit an inflammatory reaction caused by ultraviolet irradiation and protect epithelial cells.

Test Example 5. Wound Healing Promotion Test of Topical Preparation Containing Vitamin K1

1. Test purpose: wound healing promotion tests of the gel preparations containing vitamin K1 prepared in embodiment 12, embodiment 13, embodiment 14, embodiment 20, embodiment 21, embodiment 22, comparative example 5 and comparative example 6.

2. Test Method:

A total of 180 male Sprague-Dawley (SD) rats is selected, each weighing 220±20 g, followed by dividing all rats randomly into 9 groups with 20 rats in each group, marking respectively. rat hair is cut off on one side of the back spine, followed by cutting a 2 cm long and 0.2 cm deep incision with a scalpel. The gel preparations containing vitamin K1 prepared in embodiment 12, embodiment 13, embodiment 14, embodiment 20, embodiment 21, embodiment 22, comparative example 5 and comparative example 6 are applied respectively, no drug is used in the blank control group. The gel preparations are applied three times a day respectively in the morning, in the evening and in the evening, followed by observing wound healing on the 1st, 3rd, 7th and 15th day, and evaluating the wound healing by wound healing rate.

3. Test Results: The Wound Healing Rate is Shown in Table 7.

TABLE 7

Wound healing rate (%)

| | Embodiment 12 | Embodiment 13 | Embodiment 14 | Embodiment 20 | Embodiment 21 | Embodiment 22 | Comparative Example 5 | Comparative Example 6 | Blank control |
|---|---|---|---|---|---|---|---|---|---|
| Day 1 | 0.76 | 0.68 | 0.77 | 1.23 | 1.69 | 1.35 | 1.08 | 1.05 | 0.68 |
| Day 3 | 6.23 | 4.01 | 3.89 | 7.24 | 9.63 | 8.09 | 6.01 | 6.48 | 3.46 |
| Day 7 | 42.20 | 31.43 | 35.23 | 54.56 | 60.23 | 58.25 | 40.22 | 43.67 | 30.26 |
| Day 10 | 63.69 | 46.41 | 42.56 | 81.52 | 86.67 | 83.32 | 54.32 | 51.74 | 42.73 |
| Day 15 | 79.60 | 66.36 | 69.40 | 91.39 | 98.48 | 95.73 | 78.67 | 76.25 | 68.75 |

According to the data in Table 7:

(1) The wound healing rate of the gel preparations containing vitamin K1 prepared in embodiment 12, embodiment 13 and embodiment 14 is 65%-80% on the 15th day, and the wound healing rate of the gel preparations containing vitamin K1 prepared in embodiment 13 and embodiment 14 is equivalent to that of the blank control group, indicating that these two gel preparations containing vitamin K1 have no effect on promoting wound healing. The wound healing rate of the gel preparation containing vitamin K1 prepared in embodiment 12 is higher than that of the blank control group, but is equivalent to that of comparative example 5 and comparative example 6. It is suggested that the gel matrix composed of Carbopol 934P and sodium carboxymethyl cellulose has a certain effect on wound healing.

(2) The wound healing rate of the gel preparations containing vitamin K1 prepared in embodiment 20, embodiment 21 and embodiment 22 achieves more than 80% on the 10th day, and more than 90% on the 15th day. In particular, the wound healing rate of the gel preparation containing vitamin K1 prepared in embodiment 21 is as high as 98.48%, indicating that the gel preparation containing vitamin K1 in the present invention has a remarkable effect of promoting wound healing.

(3) Compared with the blank control group, the gel preparations containing vitamin K1 prepared in comparative example 5 and comparative example 6 also have a certain effect on wound healing. However, the effect on wound healing of the gel preparations containing vitamin K1 prepared in comparative example 5 and comparative example 6 on the 1st, 3rd, 7th, 10th and 15th day is worse than that of the gel preparations containing vitamin K1 prepared in embodiment 20, embodiment 21 and embodiment 22. A possible reason is that a mass ratio of Carbopol 934P and polyethylene glycol 300 in the gel matrix of the gel preparations containing vitamin K1 prepared in comparative example 5 and comparative example 6 is not in a range of (1-3):(2-3), so no dense gel layer film can be formed.

Test Example 6. Stability of Topical Preparation Containing Vitamin K1

1. Test purpose: to investigate stability of the cream preparation containing vitamin K1 prepared in embodiment 10; to investigate stability of the gel preparation containing vitamin K1 prepared in embodiment 21; to investigate stability of the cream preparations containing vitamin K1 prepared in comparative example 1 and 2; to investigate stability of the gel preparations containing vitamin K1 prepared in comparative example 3 and 4; and to investigate stability of the gel preparations containing vitamin K1 prepared in comparative examples 5 and 6.

2. Test Method:

Appearance observation: under a condition of light or without light, appearance characteristics (color) of 8 groups sample solutions, i.e., the cream preparation containing vitamin K1 prepared in embodiment 10; the gel preparation containing vitamin K1 prepared in embodiment 21; the cream preparations containing vitamin K1 prepared in comparative example 1 and 2; the gel preparations containing vitamin K1 prepared in comparative example 3 and 4; the gel preparations containing vitamin K1 prepared in comparative examples 5 and 6, are observed respectively at 0 h, 0.5 h, 1 h, 2 h, 4 h and 6 h by visual method, and the content of vitamin K1 is determined.

Content determination method: the cream preparation containing vitamin K1 and the gel preparation containing vitamin K1 under the two conditions are taken respectively, followed by dissolving in water to obtain mixed solutions, precisely adding 2.0 mL of each mixed solution at 0 h, 0.5 h, 1 h, 2 h, 4 h and 6 h respectively to a volumetric flask of 10 mL, diluting to the scale line by adding mobile phase, shaking evenly, passing through 0.22 μm microporous membrane, and then detecting by HPLC. The injection volume is 20 μL, and the wavelength is 254 nm. A peak area of each test solution is determined and substituted into a regression equation to calculate the content of each test solution. A relative percentage content of each time point is calculated by comparing measured value with the content obtained at 0 h.

3. Test Results:

In light stability test, appearance (color) and texture of samples in dark group do not change significantly, and changes in light group are shown in Table 8. Determination results of vitamin K1 content in dark and light conditions are shown in Table 9.

TABLE 8

Light stability of topical preparation containing vitamin K1

| | Embodiment 10 | Embodiment 21 | Comparative Example 1 | Comparative Example 2 | Comparative Example 3 | Comparative Example 4 | Comparative Example 5 | Comparative Example 6 |
|---|---|---|---|---|---|---|---|---|
| 0 h | Light yellow Glossy | Light yellow Glossy | Light yellow Glossy | Light yellow Glossy | Light yellow Glossy | Light yellow Glossy | Light yellow Glossy | Light yellow Glossy |
| 0.5 h | Light yellow Glossy | Light yellow Glossy | Light yellow Glossy | Light yellow Glossy | Light yellow Glossy | Light yellow Glossy | Light yellow Glossy | Light yellow Glossy |
| 1 h | Light yellow Glossy | Light yellow Glossy | Yellow Glossy | Yellow Glossy | Yellow Glossy | Yellow Glossy | Light yellow Glossy | Light yellow Glossy |
| 2 h | Yellow Glossy | Yellow Glossy | Yellow Dull | Yellow Dull | Yellow Dull | Yellow Dull | Yellow Glossy | Yellow Glossy |
| 4 h | Yellow Matte | Yellow Matte | Yellow Dull | Yellow Dull | Yellow Dull | Yellow Dull | Yellow Matte | Yellow Matte |
| 6 h | Yellow Matte | Yellow Matte | Yellow Dull | Yellow Dull | Yellow Dull | Yellow Dull | Yellow Matte | Yellow Matte |

TABLE 9

Content of vitamin K1 under dark and light conditions

| | 0 h | | 0.5 h | | 1 h | | 2 h | | 4 h | | 6 h | |
|---|---|---|---|---|---|---|---|---|---|---|---|---|
| | Light | Dark | Light | Dark | Light | Dark | Light | Dark | Light | Dark | Light | Dark |
| Embodiment 10 | 100.0 | 100.0 | 98.8 | 100.3 | 94.4 | 99.54 | 89.3 | 99.5 | 85.5 | 100.2 | 80.2 | 99.4 |
| Embodiment 21 | 100.0 | | 99.2 | 100.2 | 97.2 | 99.4 | 92.2 | 100.4 | 90.1 | 100.1 | 86.0 | 99.3 |
| Comparative Example 1 | 100.0 | | 94.2 | 98.8 | 90.2 | 99.3 | 88.9 | 99.7 | 83.5 | 98.2 | 80.1 | 99.4 |
| Comparative Example 2 | 100.0 | | 93.9 | 99.2 | 88.6 | 99.2 | 84.7 | 100.1 | 81.4 | 99.2 | 79.3 | 99.6 |
| Comparative Example 3 | 100.0 | | 96.1 | 99.4 | 88.1 | 99.2 | 85.1 | 99.3 | 81.3 | 99.8 | 80.5 | 99.7 |
| Comparative Example 4 | 100.0 | | 93.2 | 99.3 | 89.8 | 99.1 | 86.7 | 99.8 | 84.1 | 99.4 | 80.4 | 99.4 |
| Comparative Example 5 | 100.0 | | 99.0 | 99.8 | 92.9 | 99.8 | 89.7 | 100.1 | 86.6 | 99.9 | 82.2 | 99.3 |
| Comparative Example 6 | 100.0 | | 98.2 | 98.8 | 94.2 | 99.3 | 89.4 | 99.7 | 88.5 | 98.2 | 82.1 | 99.4 |

(1) Table 8 shows that the cream preparations containing vitamin K1 prepared in comparative example 1 and 2; and the gel preparations containing vitamin K1 prepared in comparative example 3 and 4 begin to yellow after being lighted for 1 h, and continuously become dimming after 2 h, 4 h and 6 h, changing from glossy at the beginning to dull; appearance of the gel preparations containing vitamin K1 prepared in comparative examples 5 and 6, the cream preparation containing vitamin K1 prepared in embodiment 10, and the gel preparation containing vitamin K1 prepared in embodiment 21 exhibit the same change with the light condition.

(2) Data in Table 9 show that the contents of vitamin K1 in topical preparations containing vitamin K1 are basically the same under dark condition. However, after being lighted, the contents of vitamin K1 in the cream preparations containing vitamin K1 prepared in comparative examples 1 and 2, the gel preparations containing vitamin K1 prepared in comparative examples 3 and 4, the cream preparation containing vitamin K1 prepared in embodiment 10, and the gel preparation containing vitamin K1 prepared in embodiment 21 decrease constantly with the extension of lighting time in 0-6 h, and at 6 h, the gel preparation containing vitamin K1 prepared in embodiment 21 has the highest vitamin K1 content, which is 86.0% (Table 9).

(3) What is more noteworthy from the data in Table 9 is that at 6 h, the contents of vitamin K1 in the cream preparation containing vitamin K1 prepared in embodiment 10 and the gel preparation containing vitamin K1 prepared in embodiment 21 are as high as 80.2% and 86.0%, the contents of vitamin K1 in the gel preparations containing vitamin K1 prepared in comparative examples 5 and 6 are also as high as 82.2% and 82.1%. There is no difference between the contents of vitamin K1 in the cream preparation containing vitamin K1 prepared in embodiment 10, the cream preparations containing vitamin K1 prepared in comparative examples 1 and 2, and the gel preparations containing vitamin K1 prepared in comparative examples 3 and 4.

(4) According to the results, the reason why the stability of the gel preparation containing vitamin K1 prepared in embodiment 21 is better than that of the cream preparation containing vitamin K1 prepared in embodiment 10 is that it contains gel matrix, the reason why the stability of the gel preparations containing vitamin K1 prepared in comparative examples 5 and 6 is slightly better than that of the cream preparations containing vitamin K1 prepared in comparative examples 1 and 2 and the gel preparations containing vitamin K1 prepared in comparative examples 3 and 4 is that it also contains gel matrix, and the gel matrix composed of Carbopol 934P and polyethylene glycol 300 in a mass ratio of (1-3):(2-3) can better maintain the stability of vitamin K1 topical preparation. It can be concluded that an addition of the gel matrix composed of Carbopol 934P and polyethylene glycol 300 according to the mass ratio (1-3):(2-3) can increase the stability of the external preparation containing vitamin K1 provided by the present invention to a certain extent.

In addition, the antioxidants provided by the present invention, including butyl hydroxyanisole, dibutylhydroxytoluene, propyl gallate, tert-butylhydroquinone, sodium sulfite, sodium bisulfite, sodium pyrosulfite and sodium thiosulfate, have a great influence on the stability of the topical preparation containing vitamin K1 of the present invention, especially antioxidant effects of fat-soluble tert-butylhydroquinone and water-soluble sodium bisulfite are more advantageous, and the stability of the topical preparation containing vitamin K1 is better when these two antioxidants are added.

The above-mentioned embodiments only illustrate the principle and efficacy of the present invention, and are not used to limit the present invention. Any person familiar with the technology can modify or change the above-mentioned embodiments without departing from the spirit and scope of the present invention. Therefore, all equivalent modifications or changes made by a person with ordinary knowledge in the technical field without departing from the spirit and technical ideas disclosed by the present invention shall still be covered by the claims of the present invention.

What is claimed is:

1. A topical preparation containing vitamin K1, comprising the following components:
   0.01-5 wt % of the vitamin K1, 0.1-25 wt % of a transdermal enhancer for promoting a penetration of the vitamin K1, and 70-99 wt % of a matrix for the topical preparation; wherein the transdermal enhancer consists of urea, menthol and *Eucalyptus* oil in a mass ratio of 5.5:2.5:2.

2. A cream preparation, comprising the topical preparation containing the vitamin K1 according to claim 1,
   wherein the matrix for the topical preparation comprises 1-25 wt % of a cream matrix, 0.2-10 wt % of an emulsifier, 2-20 wt % of a humectant, 0.05-2 wt % of an antioxidant, 0.01-1 wt % of a preservative and 10-72 wt % of water.

3. The cream preparation according to claim 2, wherein
   the cream matrix is at least one selected from the group consisting of isostearic acid, stearic acid, hexadecanol, octadecanol, glyceryl monostearate, white vaseline, lanolin and liquid paraffin;
   the emulsifier is at least one selected from the group consisting of sodium dodecyl sulfate, polysorbate 60, polysorbate 80, polyethylene glycol hydroxystearate, polyethoxylated castor oil, ethylene oxide, propylene oxide copolymer, stearoyl polyethylene glycol-32 glyceride, lauroyl polyethylene glycol-32 glyceride, propylene glycol monooctanoate and octyl acetyl polyethylene glycol-8 glyceride;
   the humectant is at least one selected from the group consisting of glycerol, propylene glycol and sorbitol;
   the antioxidant is at least one selected from the group consisting of butyl hydroxyanisole, dibutylhydroxytoluene, propyl gallate, tert-butylhydroquinone, sodium sulfite, sodium bisulfite, sodium pyrosulfite and sodium thiosulfate; and
   the preservative is at least one selected from the group consisting of hydroxyphenyl esters, trichloro tert butyl alcohol, benzyl alcohol, phenylethanol, chlorhexidine acetate, benzalkonium chloride and thiomersal.

4. A gel preparation, comprising the topical preparation containing the vitamin K1 according to claim 1,
   wherein the matrix for the topical preparation comprises 0.5-10 wt % of a gel matrix, 0.1-10 wt % of a thickener, 2-20 wt % of a humectant, 0.05-2 wt % of an antioxidant, 0.01%-1 wt % of a preservative and 40%-80 wt % of water.

5. The gel preparation according to claim 4, wherein
   the gel matrix is at least one selected from the group consisting of gelatin, copolymer of acrylic acid cross-linked polymer and polyalkyl sucrose or polyalkyl pentaerythritol, polyethylene glycol 300, methyl cellulose, sodium carboxymethyl cellulose and hydroxypropyl methylcellulose; and
   the thickener is at least one selected from the group consisting of xanthan gum, carrageenan and Brunei gum.

6. The gel preparation according to claim 5, wherein the gel matrix is composed of the copolymer of acrylic acid cross-linked polymer and polyalkyl sucrose or polyalkyl pentaerythritol and the polyethylene glycol 300 in a mass ratio of (1-3):(2-3).

7. The gel preparation according to claim 4, wherein the humectant is at least one selected from the group consisting of glycerol, propylene glycol and sorbitol.

8. The gel preparation according to claim 4, wherein
   the antioxidant is at least one selected from the group consisting of butyl hydroxyanisole, dibutyl hydroxytoluene, propyl gallate, tert-butylhydroquinone, sodium sulfite, sodium bisulfite, sodium pyrosulfite and sodium thiosulfate; and
   the preservative is at least one selected from the group consisting of hydroxyphenyl esters, trichloro tert butyl alcohol, benzyl alcohol, phenylethanol, chlorhexidine acetate, benzalkonium chloride and thiomersal.

* * * * *